US00PP13505P2

(12) United States Plant Patent
Zaiger et al.

(10) Patent No.: US PP13,505 P2
(45) Date of Patent: Jan. 21, 2003

(54) INTERSPECIFIC TREE NAMED 'ROYAL TREAT'

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/067,637

(22) Filed: Feb. 7, 2002

(51) Int. Cl.[7] ..... A01H 5/00
(52) U.S. Cl. ..... Plt./180
(58) Field of Search ..... Plt./180

*Primary Examiner*—Bruce R. Campbell
*Assistant Examiner*—Anne Marie Grünberg

(57) ABSTRACT

A new and distinct variety of interspecific tree (Plum× Plumcot). The following features of the tree and its fruit are characterized with the tree budded on 'citation' Rootstock (U.S. Plant Pat. No. 5,112), grown on Handford sandy loam soil with Storie Index rating 95, in USDA Hardiness Zone 9, near Modesto, Calif., with standard commercial fruit growing practices such as pruning, thinning, spraying, irrigation and fertilization. Its novelty consists of the following combination of desirable features:

1. Fruit with very good flavor and eating quality.
2. Fruit maturing in the early maturity season.
3. Fruit with an attractive dark magenta skin color.
4. Vigorous, upright growth habit.
5. Fruit with a good balance between sugar and acid, having soluble solids of 14.8° Brix.

1 Drawing Sheet

STATEMENT REGARDING FEDERALLY SPONSORED RESEARCH OR DEVELOPMENT

Not applicable.

BACKGROUND OF THE VARIETY

Field of the Invention

In the field of plant genetics, we conduct an extensive and continuing plant-breeding program including the organization and asexual reproduction of orchard trees, and of which almonds, plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum trees (*Prunus salicina*), which are known to us, and mentioned herein, 'Laroda' Plum (non-patented), 'Queen Ann' Plum (non-patented) and the Interspecific tree 'Citation' (U.S. Plant Pat. No. 5,112), (*Prunus salicina×Prunus persica*).

ORIGIN OF THE VARIETY

The new interspecific Prunus tree [*Prunus salicina*× (*Prunus salicina×Prunus armeniaca*)] originated in our experimental orchard, located near Modesto, Calif., as a cross between our proprietary parent labeled 33ED7 with a plumcot of unknown parentage. The maternal parent 33ED7 originated from a cross of 'Laroda' Plum (non-patented) with 'Queen Ann' Plum (non-patented). A large group of these seedlings were grown, on their own root system, under close and careful observation, during which time one seedling, which is the present variety, exhibited desirable fruit characteristics and, in 1992, was selected for asexual propagation and commercialization.

ASEXUAL REPRODUCTION OF THE VARIETY

Asexual reproduction of the new and distinct variety of interspecific tree was by budding, in 1992, to 'Citation' Rootstock (U.S. Plant Pat. No. 5,112), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new interspecific tree (Plum×Plumcot) is of large size, vigorous, upright growth and a regular and productive bearer of medium size, yellow flesh fruit with very good flavor and eating quality. The fruit is further characterized by being relatively uniform in size throughout the tree, having firm flesh with good handling and shipping quality and maturing in the early maturity season. In comparison to one of its maternal parents,'Laroda' Plum (non-patented), the fruit of the new variety is more uniform in size, has flesh with uniformly yellow color, compared to the amber color with reddish bleeding near the skin and is approximately 30 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of color.

Tree:

*Size.*—Large. Pruned to 3 to 3.5 meters in height and width, primarily for economical harvesting of fruit.

*Vigor.*—Vigorous. Growth of 1.5 to 2 meters in height the first growing season. Varies with type of soil, fertility and climatic conditions.

*Growth.*—Upright, similar to standard plums. Pruned to vase shape.

*Branching habit.*—Upright. Crotch angle approximately 30°, increases with heavy production of fruit.

*Productivity.*—Heavy. Usually sets 1½ to several times more fruit than desired, thinning and spacing of fruit necessary.

*Bearer.*—Regular. Adequate fruit set 4 consecutive years, no alternate bearing observed.

*Fertility.*—Self-sterile, pollenizer required.

*Density.*—Medium dense. Usually pruned to vase shape by removing branches from center of tree to allow more sunlight and air movement to enhance fruit color and health of fruit spurs.

*Hardiness.*—Hardy in all stone fruit growing areas of California. Winter chilling requirement approximately 700 hours at or below 45° F. Grown in USDA Hardiness Zone 9 near Modesto, Calif.

Trunk:

*Size.*—Large, stocky. Average circumference 50.8 cm at 21.5 cm above ground on a 6 year old tree.

*Surface.*—Medium shaggy, increases with age.

*Color.*—Varies from 10R 6/2 to 5YR 5/2.

Branches:

*Size.*—Medium to large. Average circumference 16.4 cm at 1.5 meters above ground. Crotch angle approximately 30°, increases with heavy crop load.

*Surface texture.*—New growth smooth. Mature growth is moderately rough.

*Lenticels.*—Color 2.5YR 7/8. Average number 31 in a 25.8 square cm surface. Average length 2.34 mm. Average width 0.74 mm.

*Color.*—New growth 2.5GY 8/6 to 2.5GY 8/8. Older growth 5YR 4/4 to 5YR 4/6, varies with age of growth.

Leaves:

*Size.*—Large. Average length 113.7 mm. Average width 53.7 mm.

*Form.*—Oblanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins, glabrous. Lower surface relatively smooth, small ridges created by midrib and pinnate venation, glabrous.

*Petiole.*—Average length 12.8 mm. Average width 2 mm. Color 5GY 8/6. Grooved longitudinally.

*Glands.*—Globose. Small. Average length 0.7 mm. Average diameter 0.4 mm. Number varies from 1 to 5, average number 3. Located on upper portion of petiole and base of leaf blade.

*Color.*—Upper surface 5GY 4/4. Lower surface 5GY 5/4. Midvein color 5GY 8/4.

*Flower buds.*—Small to medium, varies with degree of maturity. Average length 12.2 mm. Average diameter 5 mm.

*Hardiness.*—Hardy in all stone fruit growing areas of California. Grown in USDA Hardiness Zone 9 near Modesto, Calif.

*Form.*—Plump, conical, becoming elongated before opening, glabrous.

*Pedicel.*—Average length 10.1 mm. Average width 0.7 mm. Color 2.5GY 7/8.

*Color.*—N 9/0.5.

*Number of buds per spur.*—Usually 4, varies from 3 to 8.

Flowers:

*Size.*—Medium to large. Average height 13.9 mm. Average diameter 20.4 mm.

*Petals.*—alternately arranged to sepals. Elliptic shape. Average length 10.5 mm. Average width 6.1 mm. Margin — entire, slightly cupped near apex. Color — N 9/.5.

*Sepals.*—5, alternately arranged to petals. Shape — ovate. Both surfaces glabrous. Average length 3.2 mm, apex rounded. Average width 3.3 mm. Color — upper surface 5GY 5/6, lower surface 5GY 6/10.

*Stamens.*—Average number per flower — 36. Average filament length 7.1 mm. Filament color N 9/.5. Anther color 8.75R 4/14.

*Pollen.*—Abundant. Color 1.25Y 7/12. Self-sterile, pollenizer required.

*Pistil.*—Usually one. Average length 10.8 mm. Stigma approximately 1.33 mm above anthers. Glabrous. Color 2.5GY 9/6.

*Fragrance.*—Moderate aroma.

*Blooming period.*—Date of First Bloom Feb. 28, 2001. Date of Petal Fall Mar. 14, 2001. Varies slightly with climatic conditions.

*Color.*—N9/.5.

*Number of flowers per flower bud.*—Usually 2, varies from 1 to 3.

*Pedicel.*—Average length 14.1 mm. Average width 0.8 mm. Color — 2.5GY 7/12.

Fruit:

*Maturity when described.*—Firm ripe.

*Date of first picking.*—Jun. 8, 2001.

*Date of last picking.*—Jun. 14, 2001. Varies slightly with climatic conditions.

*Size.*—Average diameter axially 49.1 mm. Average transversely in suture plane 57.3 mm. Average weight 89.7 grams. Average weight varies slightly with fertility of the soil, amount of thinning and climatic conditions.

*Form.*—Nearly globose. Slightly flattened at apex and base.

*Suture.*—Very shallow, extends from base to apex.

*Ventral surface.*—Relatively smooth.

*Apex.*—Slightly retuse, nearly flat.

*Base.*—Retuse.

*Cavity.*—Rounded, slightly elongated in suture plane. Average depth 4.2 mm. Average width 7.9 mm.

Stem:

*Size.*—Average length 14.4 mm. Average diameter 1.9 mm.

*Color.*—Varies from 2.5GY 7/8 to 2.5GY 7/10, varies slightly with amount of surface exposed to sunlight.

Flesh:

*Ripens.*—Evenly.

*Texture.*—Firm, meaty.

*Fibers.*—Few, small, tender.

*Firmness.*—Firm, comparable to 'Laroda' Plum (non-patented).

*Aroma.*—Slight.

*Amydgalin.*—Undetected.

*Eating quality.*—Very good.

*Flavor.*—Very good, mild, sweet.

*Juice.*—Moderate, enhances flavor.

*Brix.*—14.8°, varies slightly with amount of fruit per tree and climatic conditions.

*Color.*—Varies from 7.5Y 9/4 to 7.5Y 9/6. Pit color — 5Y 6/8.

Skin:

*Thickness.*—Medium, tenacious to the flesh.

*Surface.*—Smooth.

*Bloom.*—Moderate amount, complete coverage.

*Tendency to crack.*—None.

*Color.*—Ground color 5Y 8/6 to 5Y 8/8, overspread with 2.5R 2/6 to 5R 2/6. Very small, randomly spaced, areas of ground color exposed to give speckled pattern to skin in some areas.

*Astringency.*—Undetected.

Stone:

*Type.*—Clingstone.

*Size.*—Medium. Average length 19 mm. Average width 19.6 mm. Average thickness 9.5 mm.

*Form.*—Obovate.

*Base.*—Varies from rounded to straight.

*Apex.*—Acuminate. Short, 1.8 mm.

*Surface.*—Very lightly pitted throughout. Usually 3 to 4 small, narrow ridges of various length running from base toward apex. One shallow groove on each side of suture.

*Sides.*—Varies from equal to unequal with one side of stone extending further from suture plane.

*Tendency to split.*—None.

*Color.*—5YR 7/6 when dry.

Kernal:

*Form.*—Ovate.

*Taste.*—Bitter.

*Viable.*—Complete embryo development.

*Size.*—Medium. Average length 10.5 mm. Average width 9.4 mm. Average thickness 4.3 mm.

*Skin color.*—10YR 7/10, when dry.

Use: Dessert. Market — local and long distance.

Keeping quality: Good, held firm for 2 weeks in cold storage at 38° to 42° F. without internal flesh breakdown or loss of flavor.

Shipping quality: Good picking, packing and shipping trials showed minimal skin scarring or flesh bruising of fruit.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, vigorous, upright growth and being a productive and regular bearer of medium size, yellow flesh, clingstone fruit with very good flavor and eating quality. The fruit is further characterized by ripening in the early maturing season and, in comparison to the 'Laroda' Plum (non-patented), the fruit is approximately 30 days earlier in maturity.

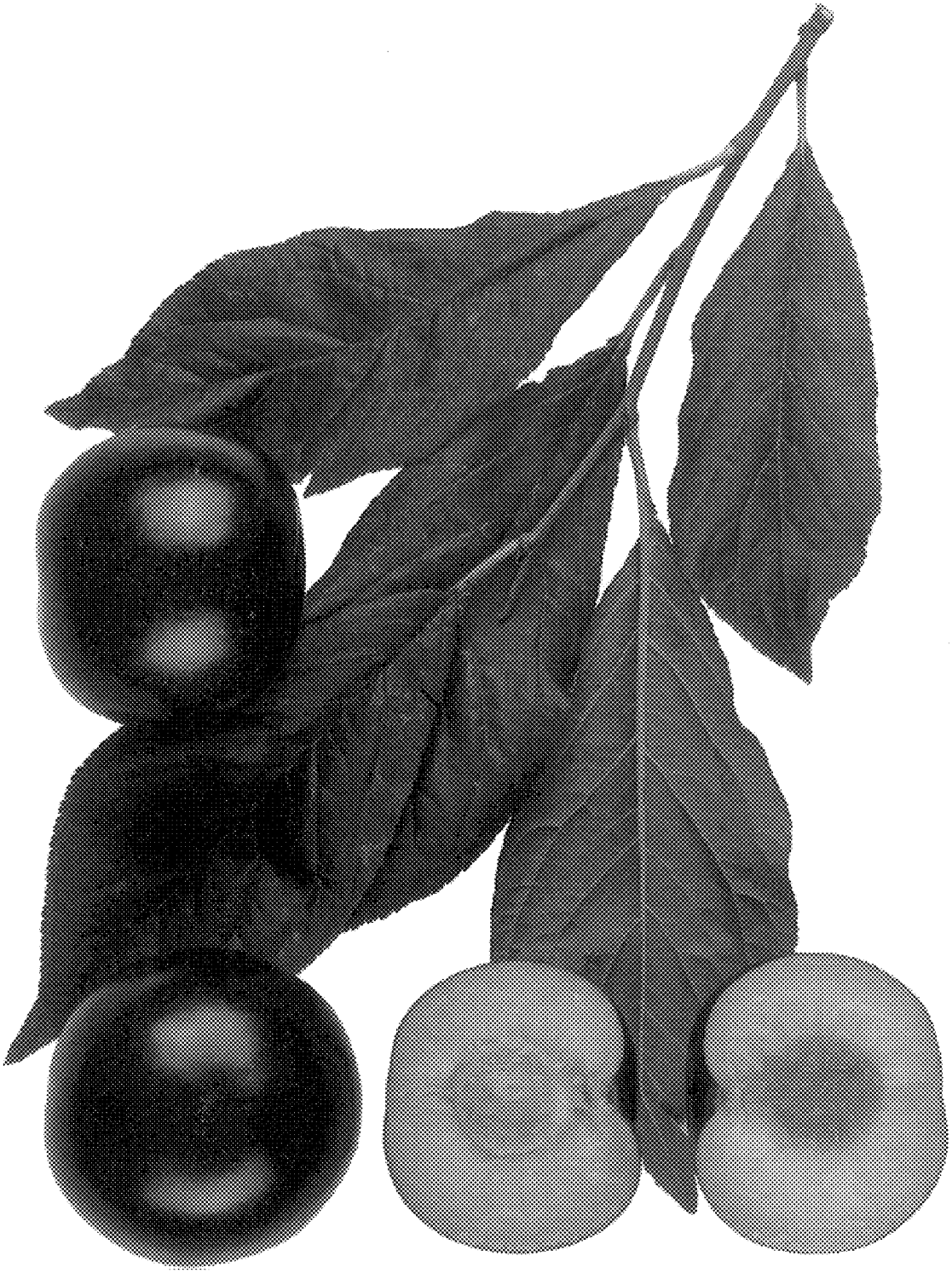

* * * * *